United States Patent
Yakabe (10) Patent No.: US 7,368,920 B2
(45) Date of Patent: May 6, 2008

(54) POTENTIAL FIXING DEVICE AND POTENTIAL FIXING METHOD

(75) Inventor: Masami Yakabe, Tokyo (JP)

(73) Assignee: Tokyo Electron Limited, Tokyo (JP)

( * ) Notice: Subject to any disclaimer, the term of this patent is extended or adjusted under 35 U.S.C. 154(b) by 436 days.

(21) Appl. No.: 10/488,597

(22) PCT Filed: Sep. 6, 2002

(86) PCT No.: PCT/JP02/09084

§ 371 (c)(1),
(2), (4) Date: Oct. 4, 2004

(87) PCT Pub. No.: WO03/023418

PCT Pub. Date: Mar. 20, 2003

(65) Prior Publication Data

US 2005/0030679 A1    Feb. 10, 2005

(30) Foreign Application Priority Data

Sep. 6, 2001   (JP) ............................. 2001-270491

(51) Int. Cl.
*G01R 27/26* (2006.01)
(52) U.S. Cl. .................. 324/658; 324/662; 324/663
(58) Field of Classification Search ................ 324/663, 324/662, 658
See application file for complete search history.

(56) References Cited

U.S. PATENT DOCUMENTS

| | | | | |
|---|---|---|---|---|
| 3,648,165 A | * | 3/1972 | Shawhan | 324/677 |
| 3,774,238 A | * | 11/1973 | Hardway, Jr. | 324/663 |
| 5,028,876 A | * | 7/1991 | Cadwell | 324/678 |
| 5,659,264 A | | 8/1997 | Ariyoshi et al. | |
| 6,630,834 B2 | * | 10/2003 | Min et al. | 324/676 |
| 2005/0116700 A1 | | 6/2005 | Yakabe et al. | |

(Continued)

FOREIGN PATENT DOCUMENTS

DE    3428699 A1    2/1986

(Continued)

OTHER PUBLICATIONS

Supplementary European Search Report, no date provided.

*Primary Examiner*—Andrew H. Hirshfeld
*Assistant Examiner*—John Zhu
(74) *Attorney, Agent, or Firm*—Finnegan, Henderson, Farabow, Garrett & Dunner LLP (57) ABSTRACT

An electric potential fixing apparatus of the present invention is an electric potential fixing apparatus that is connected to a connection line (17) between two capacitances, the first capacitance (14) and the second capacitance (15) that is directly connected to the first capacitance, includes the first high resistance (3), the second high resistance (4) that is connected directly to the first high resistance, a voltage dividing unit that outputs electric potential divided by the first high resistance and the second high resistance to the output terminal, the third capacitance (8) that is connected in parallel to at least either of the first high resistance and the second high resistance, and a voltage supply unit (1) operable to maintain constantly electric potential of the connection line between the two capacitances (14) and (15), holding combined total electric charge quantity of the first capacitance and the second capacitance, and the output terminal of the voltage supply unit is connected to a signal line between the two capacitances.

7 Claims, 3 Drawing Sheets

FOREIGN PATENT DOCUMENTS

| | | |
|---|---|---|
| DE | 40 14 395 A1 | 11/1991 |
| JP | 63-015505 | 1/1988 |
| JP | 11-097977 | 4/1999 |
| JP | 2002-323523 | 11/2002 |
| WO | WO 94/23547 | 10/1994 |

* cited by examiner

POTENTIAL FIXING DEVICE AND POTENTIAL FIXING METHOD

TECHNICAL FIELD

The present invention relates to a capacitance measurement apparatus to measure a capacitance value of a capacitive sensor whose electrostatic capacitance changes in response to received physical quantity and particularly to the capacitance measurement apparatus equipped with an electric potential fixing/standard capacitance cancel circuit that fixes electric potential of a signal line in the capacitance measurement apparatus and cancels standard capacitance of a capacitive sensor.

BACKGROUND ART

Figure 1:
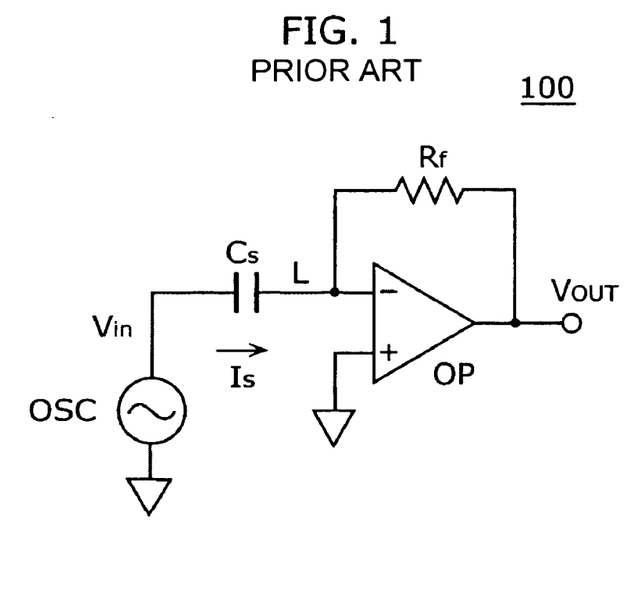
FIG. 1 is a circuit diagram that shows a conventional capacitance measurement apparatus.

Conventionally, a capacitance measurement apparatus that measures a capacitance value of a capacitive sensor such as a capacitor microphone whose electrostatic capacitance changes in response to received physical quantity (acceleration, pressure, gas, light, sound wave and so on) is known. FIG. 1 shows a conventional capacitance measurement apparatus 100. As shown in FIG. 1, the conventional capacitance measurement apparatus 100 includes an operational amplifier OP, an AC voltage generation apparatus OSC, a capacitive sensor $C_s$, resistance $R_f$ that is feedback impedance. The AC voltage generation apparatus OSC generates an operation signal $V_{in}$ that is applied to the capacitive sensor $C_s$ at the time of measuring the capacitance. The capacitive sensor $C_s$ and an inversion input terminal of the operational amplifier OP are connected by the signal line L. The resistance $R_f$ is connected between the signal line L and the operational amplifier OP. Additionally, the capacitive sensor $C_s$ is connected between the inversion input terminal of the operational amplifier OP and the AC voltage generation apparatus OSC. One terminal of the AC voltage generation apparatus OSC is connected to standard electric potential.

As for an operation of the conventional capacitance measurement apparatus 100 shown in FIG. 1, when voltage $V_{in}$ from the AC voltage generation apparatus OSC is supplied, alternating current flows to the capacitive sensor $C_s$. In this case, since input impedance of the operational amplifier OP is ideally infinite, all the current that flows to the capacitive sensor $C_s$ flows to the resistance $R_f$.

Output of the capacitance measurement apparatus $V_{out}$ can be derived from the following method.

When the amplitude of the operation signal is V, the angular velocity of the operation signal is $\omega_{in}$, the standard capacitance of the capacitive sensor is $C_d$, the amplitude of change capacitance of the capacitive sensor $C_s$ is C, and the angular velocity of capacitance change is $\omega_c$, the operation signal $V_{in}$ and the capacitance of the capacitive sensor $C_s$ can be represented by $$V_{in} = V \sin \omega_{in} t \qquad (1)$$

$$C_s = C_d + C \sin \omega_c t \qquad (2)$$

Since the current $I_s$ that flows through the capacitive sensor can be represented by $$I_s = d(C_s V_{in})/dt \qquad (3)$$

and the output $V_{out}$ can be represented by $$V_{out} = -I_s R_f \qquad (4),$$

by the expressions (1) through (4)

$$V_{out} = -R_f\{(C_d + C \sin \omega_c t)\cdot\omega_{in}\cdot\cos \omega_{in} t + C\cdot\omega_c\cdot\cos \omega_c t\cdot\sin \omega_{in} t\}V \qquad (5)$$

is derived.

As is known from this expression (5), the output $V_{out}$ has a term whose coefficient is the angular velocity of the capacitance change $\omega_c$. This means that in the case of the feedback impedance being the resistance, when the capacitance of the capacitive sensor changes at the frequency $\omega_c$, the output $V_{out}$ that depends on the frequency $\omega_c$ is outputted (the output $V_{out}$ has frequency dependence). Consequently, in the case of the feedback impedance being the resistance, a processing circuit that does not have a frequency characteristic in the subsequent stage must be configured, and therefore there is a problem that the size of the circuit becomes large.

Figure 2:
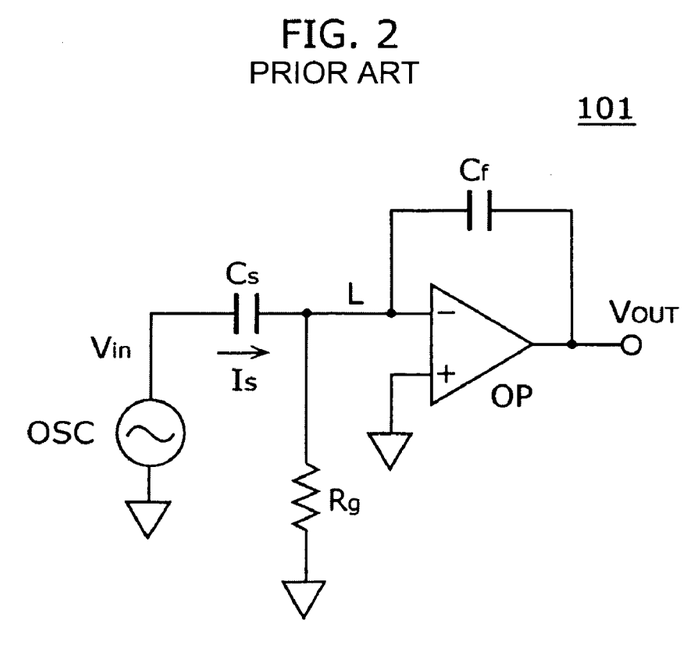
FIG. 2 is a circuit diagram that shows an electric potential fixing method as a comparative example.

There, technology that the feedback impedance is configured not by the resistance but by the capacitance is proposed. FIG. 2 shows the capacitance measurement apparatus 101 whose feedback impedance is configured by the capacitance $C_f$. In this case, since the electric charge stored in the capacitive sensor $C_s$ and that stored in the feedback capacitance $C_f$ are equal, $$-C_f V_{out} = C_s \cdot V_{in} \qquad (6)$$

holds, and therefore the output $V_{out}$ can be represented by $$V_{out} = -(C_d + C \sin \omega_c t)/C_f \cdot V \sin \omega_{in} \qquad (7)$$

As is known from this expression, output voltage $V_{out}$ does not include a term that is proportional to the angular velocity $\omega c$. This is because the electric charge of the signal line L that is connected to two capacitances is maintained constantly when the feedback impedance is configured by the capacitance.

As described above, since the term that is proportional to frequency of capacitance change dose not appear in circuit output, there is no need to set up a processing circuit newly in the subsequent stage. As a result, it is possible to prevent the size of the circuit from becoming large.

However, in the case of configuring the feedback impedance by the capacitance $C_f$, the signal line L that connects $C_f$ and the capacitive sensor becomes floating state electrically. For this reason, the electric potential of the signal line L becomes unstable and abnormality in a circuit operation that the circuit output is saturated with the power voltage may occur.

To prevent such a circuit abnormality, as shown in FIG. 2, it is conceivable to fix the electric potential of the signal line L by connecting resistance $R_g$ between the signal line L and the ground.

However, in the case of fixing the electric potential by the resistance $R_g$, at the time of measuring the capacitance, there may be a case that potential difference in the both terminals of the resistance $R_g$ is generated and that current flows through the resistance $R_g$. In that case, since the amount of electric charge varies in quantity, there is a problem that the sensibility of the capacitance measurement apparatus 101 decreases.

Consequently, it is desirable to propose a means to fix the electric potential of the signal line L without changing the electric charge quantity of the signal line L.

Additionally, when the standard capacitance $C_d$ of the capacitive sensor $C_s$ is very large compared with the capacitance change C, there is a problem that the capacitance change is not fully reflected in the output $V_{out}$.

Consequently, even if the standard capacitance $C_d$ is very large compared with the capacitance change C, a circuit with satisfactory sensibility is desirable.

The present invention is done to solve the above-mentioned problems and the object of the present invention is to provide a capacitance measurement apparatus equipped with an electric potential fixing means for fixing the electric potential level of the signal line without changing the electric charge quantity of the signal line of the capacitance measurement apparatus and a standard capacitance cancel means for canceling the effect that the standard (fixed) capacitance of the capacitive sensor has on the circuit output.

DISCLOSURE OF INVENTION

An electric potential fixing apparatus in one aspect of the present invention is an electric potential fixing apparatus that is connected to a connection line between two capacitances, a first capacitance and a second capacitance that is directly connected to the first capacitance comprising: an output terminal that is connected to the connection line; a voltage supply unit operable to maintain constantly electric potential of the connection line between the two capacitances, holding combined total electric charge quantity of the first capacitance and the second capacitance by supplying voltage to the connection line from the output terminal, wherein the voltage supply unit includes a first high resistance and a second high resistance that is directly connected to the first high resistance; a voltage dividing unit that outputs electric potential divided by the first high resistance and the second high resistance to the output terminal; and a third capacitance that is connected in parallel to at least either of the first high resistance and the second resistance.

Here, it is desirable to connect the first high resistance and the second high resistance in series. By the way, the high resistance in this invention can be realized using a reverse bias characteristic of diode and the off state of a transistor.

The electric potential fixing apparatus in the other aspect of this invention is an electric potential fixing apparatus that is connected to a connection line between two capacitances, a first capacitance and a second capacitance that is directly connected to the first capacitance comprising: an output terminal that is connected to the connection line; a voltage supply unit operable to output, to the connection line, electric potential that is equal to electric potential of an operation signal applied to the connection line; wherein the voltage supply unit includes a first high resistance and a second high resistance that is directly connected to the first high resistance; a voltage dividing unit that outputs electric potential divided by the first high resistance and the second high resistance to the output terminal; and a third capacitance that is connected in parallel to at least either of the first high resistance and the second high resistance.

Hereby, since entrance and exit of the electric current from the first high resistance and the second high resistance into the connection line is stopped, the electric charge of the connection line is maintained. In this way, since the electric charge of the connection line is maintained, for example, in a capacitance measurement apparatus, in the case of fixing the electric potential of the connection line of the first capacitance and the second capacitance, the sensibility of the capacitance measurement apparatus does not decrease. As a result, it is possible to execute an accurate capacitance measurement. Additionally, it is possible to easily adjust output electric potential of the voltage supply means by selecting appropriately the resistance values of the first high resistance and the second high resistance. By the way, it is desirable to connect the first high resistance and the second high resistance in series. Here, a high resistance means a resistance that has a sufficiently large and relatively high resistance value compared with the impedance components of the first capacitance and the second capacitance. Additionally, when the high resistance is viewed from a different aspect, it is possible to say that it has a nature that the input impedance of the electric potential fixing unit viewed from the connection line is larger than the input impedance to a circuit including either the first capacitance or the second capacitance viewed from the connection line.

Further, in the electric potential fixing apparatus in one aspect or the other aspect, it is desirable that the voltage supply unit further includes an amplifier and a predetermined voltage applying unit, the amplifier is connected to a terminal of the first high resistance, the other terminal of the first high resistance and a terminal of the second high resistance are connected, the output terminal is connected between the other terminal of the first high resistance and the terminal of the second high resistance, and the other terminal of the second high resistance and the predetermined voltage applying unit are connected each other.

When configured like this, by deciding the amplitude of the amplifier, the resistance values of the first fixed resistance and the second fixed resistance, and the voltage value of the predetermined electric potential applying unit, it is possible to easily control the electric potential of the output terminal of the voltage supply unit to be the same electric potential as the electric potential of the operation signal applied to the connection line between the first capacitance and the second capacitance. Furthermore, by deciding the amplification factor of the amplifier, the capacitance value of the capacitance to cancel the standard capacitance, it is possible to easily control the supply quantity from the capacitance to cancel the standard capacitance out of the electric current that flows through the first capacitance.

The electric potential fixing apparatus in one aspect or the other aspect further comprises a first operational amplifier, the first capacitance is a measuring capacitance, the connection line between the two capacitances is a signal line, and the input terminal of the first operational amplifier is connected to the signal line.

Additionally, the electric potential fixing apparatus in one aspect or the other aspect further comprises the second operational amplifier, and the output terminal of the second operational amplifier is connected to the second capacitance.

An electric potential fixing method in one aspect of this invention is an electric potential fixing method for fixing electric potential of a connection line between two capacitances, a first capacitance and a second capacitance that is directly connected to the first capacitance, using a voltage supply unit which has an amplifier, a third capacitance, and at least two high impedances that divide the voltage, the third capacitance being connected with at lest one of the high impedances, the electric potential fixing method including: a step for applying output of the voltage supply unit to the connection line between the two capacitances; and a step for deciding fixed electric potential of a connection line by adjusting an amplitude of the amplifier and a capacitance value of the third capacitance.

Note that the high impedance and the high resistance have the same function.

The electric potential fixing method in the other aspect of this invention is an electric potential fixing method for fixing electric potential of a connection line between two capacitances, a first capacitance and a second capacitance that is directly connected to the first capacitance, using a voltage supply unit which has an amplifier, a first high resistance and a second high resistance, and a third capacitance that is connected in parallel to at least either of the first high resistance and the second high resistance, the electric potential fixing method including; a step for outputting electric potential divided by the first high resistance and the second high resistance to the connection line between the two capacitances; a step for setting up electric potential of an operation signal that is applied to the connection line between the two capacitances and output electric potential of the voltage supply unit to become equal by adjusting an amplitude of the amplifier, values of the two high resistances and a value of a third capacitance.

It is desirable that in the electric potential fixing method in one aspect or the other aspect of this invention, a terminal part of either the first high resistance or the second high resistance of the voltage supply unit includes a predetermined voltage applying unit, and the electric potential of an operation signal that is applied to the connection line between the two capacitances and the output electric potential of the voltage supply unit are set up to become equal by adjusting applied voltage of the predetermined voltage applying unit.

Additionally, the electric potential fixing method in one aspect or the other aspect uses either the first capacitance or the second capacitance as a measuring capacitance.

BEST MODE FOR CARRYING OUT THE INVENTION

Figure 3:
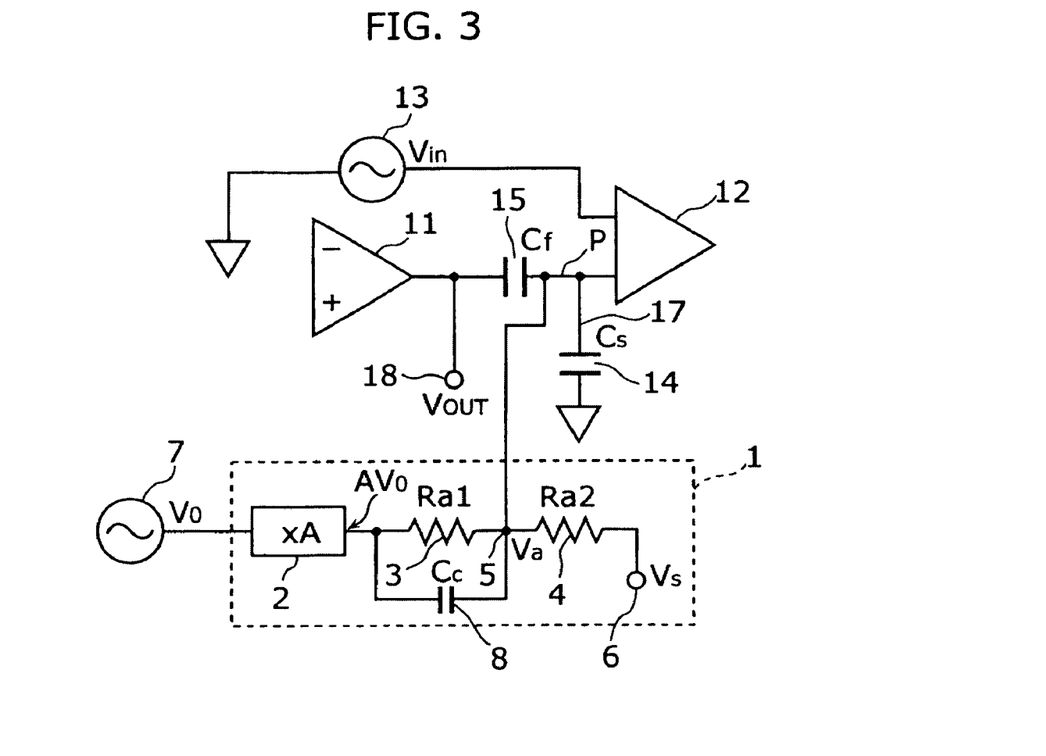
FIG. 3 is a circuit diagram that shows a capacitance measurement apparatus including an electric potential fixing apparatus according to the first embodiment of the present invention.

FIG. 3 is a circuit diagram that shows a capacitance measurement apparatus including an electric potential fixing apparatus according to the first embodiment of the present invention.

For a start, referring to FIG. 3, the configuration of the capacitance measurement apparatus including the electric potential fixing apparatus according to the first embodiment is explained. The capacitance measurement apparatus according to the first embodiment includes an operational amplifying circuit 11 that is a voltage generator to acquire a gain, an operational amplifier 12 in a state of imaginary short, an AC voltage generator 13, a measuring capacitance 14, and a feedback capacitance 15. By the way, the operational amplifier 12 is an example of "the first operational amplifier" of the present invention and the operational amplifying circuit 11 is an example of "the second operational amplifier" of the present invention. Additionally, the measuring capacitance 14 is an example of "the first capacitance" or "the second capacitance" of the present invention and its capacitance value $C_s$ is represented by an addition of the standard capacitance $C_d$ and the change capacitance C sin $\omega_c$t, namely, $C_s = C_d + C$ sin $\omega_c$t. The standard capacitance is the capacitance that the first capacitance and the second capacitance own characteristically and the fixed capacitance value before external force is added. The feedback capacitance 15 is an example of "the first capacitance" or "the second capacitance" of the present invention. The measuring capacitance 14 and the feedback capacitance 15 are connected by a signal line 17. In addition, this signal line 17 is an example of "a connection line" of the present invention. The terminal of the detecting capacitance 14 that is not connected to the signal line may be in a state of floating but it is possible to measure with high accuracy when the end of the measuring capacitance 14 is connected to the predetermined electric potential. The signal line 17 is connected to an input terminal of the operational amplifier 12. Furthermore, the AC voltage generator 13 is connected to the other input terminal of the operational amplifier 12.

Here, in the first embodiment, the electric potential of the signal line 17 is fixed using the electric potential fixing apparatus equipped with a voltage supply circuit 1. Note that the voltage supply circuit 1 is an example of "a voltage supply means" of the present invention. The voltage supply circuit 1 includes an amplifier 2 that has an amplitude A, the first high resistance 3 that has a resistance value of $R_{a1}$, the second high resistance 4 that has a resistance value of $R_{a2}$, and a capacitance to cancel the standard capacitance 8 that has a capacitance value of $C_c$. It is acceptable if $R_{a1}$ of the first high resistance 3 and $R_{a2}$ of the second high resistance are the resistance values that have sufficiently high values relatively compared with an approximate characteristic impedance value obtained by the frequency and the detected capacitance used together. By the way, a variant A that is indicated by A times and so on in the present invention is a real number except 0.

Moreover, to the input side of the amplifier 2 is connected a different AC voltage generator (another power) 7 from the AC voltage generator 13. To the output side of the amplifier 2 is connected one terminal of the first high resistance 3. Between the other terminal of the first high resistance 3 and one terminal of the second high resistance 4 is connected an output terminal 5. The output terminal 5 of the voltage supply circuit 1 is connected to the signal line 17 at the point P. A terminal 6 is set up to the other terminal of the second high resistance 4. To the terminal 6 is applied the predetermined electric potential $V_s$. This terminal 6 is an example of "the predetermined voltage applying means". Additionally, from the output terminal 5 is outputted Voltage Va divided by the resistance partition of the first high resistance 3 and the second high resistance 4.

Figure 4:
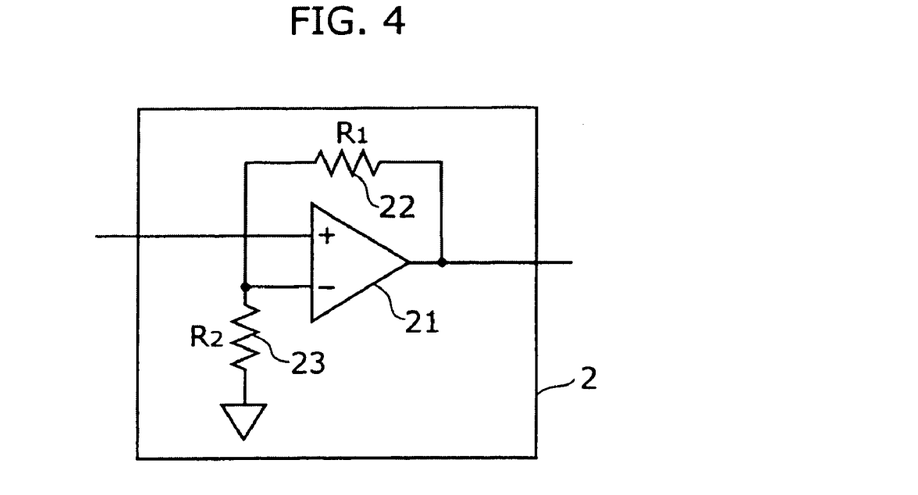
FIG. 4 is a circuit diagram that shows an example of an internal configuration of an amplifier included in the electric potential fixing apparatus according to the first embodiment shown in FIG. 3.

Additionally, the amplifier 2, for example, has a configuration shown in FIG. 4. Namely, the amplifier 2 includes an operational amplifier 21, a resistance 22 that has a resistance value of $R_1$, and a resistance 23 that has a resistance value of $R_2$. To the non-inverting input terminal of the operational amplifier 21 is connected the AC voltage generator 7 (refer to FIG. 3). Furthermore, between the output terminal and the non-inverting input terminal of the operational amplifier 21 is connected the resistance 22. Moreover, between the non-inverting input terminal of the operational amplifier 21 and GND is connected the resistance 23. When configured like this, it is possible to obtain easily the amplifier 2 that has an amplitude $A=(R_1+R_2)/R_2$.

As for the electric potential fixing method of the capacitance measuring apparatus according to the first embodiment, the amplitude A of the amplifier 2, the resistance $R_{a1}$ of the first high resistance 3, the resistance $R_{a2}$ of the second high resistance 4, and the voltage V of the terminal 6 $V_s$ are decided in order that the voltage $V_{in}$ of the operation signal that flows through the signal line 17 and the voltage $V_a$ of the output terminal 5 of the voltage supply circuit 1 become equal. The capacitance value $C_c$ of the capacitance to cancel the standard capacitance 8 as the third capacitance and the amplitude A of the amplifier 2 are decided in order to supply at least part of the current that flows through the measuring capacitance 14.

As for the capacitance measurement operation of the capacitance measurement apparatus of the first embodiment shown in FIG. 3, since the operational amplifier 12 is in the state of imaginary short, the voltage $V_{in}$ (of the operation signal) from the AC voltage generator 13 is applied to the signal line 17. By so doing, the voltage is applied to the both terminals of the measuring capacitance 14 and the current flows. Then, the output $V_{out}$ that corresponds to electrostatic capacitance $C_s$ of the measuring capacitance 14 is outputted from the signal output terminal 18. By executing various kinds of signal processing on this output voltage $V_{out}$, the electrostatic capacitance $C_s$ of the measuring capacitance 14 is obtained.

In the first embodiment, as is described above, the voltage supply circuit 1 that applies the alternating current in order to fix the electric potential and cancel the standard capacitance to the signal line 17 that connects the measuring capacitance 14 and fixed capacitance 15, by setting up the amplitudes A, $R_{a1}$, and $R_{a2}$ of the amplifier 2 in order that the electric potential of the output terminal 5 of the voltage supply circuit 1 determined by dividing pressure of the output of the amplifier 2 with the first high resistance 3 and the second resistance 4 becomes equal to the electric potential $V_{in}$ of the operation signal that is applied to the signal line 17, entrance and exit of the electric current from the first high resistance 3 and the second high resistance 4 into the signal line 17 is stopped and the electric charge quantity is prevented from changing. Additionally, by including the first high resistance 3 and the second high resistance 4 that have high impedance values in the voltage supply circuit 1, it is possible to effectively prevent part of the electric current that flows through the signal line 17 from flowing into the voltage supply circuit 1. This also can prevent the electric charge quantity of the signal line 17 from changing. In addition, by supplying at least a part of electric current that flows through the measuring capacitance 14 from the amplifier 2 through the capacitance to cancel the standard capacitance 8, the electric current supplied from the operational amplifying circuit 11 through the feedback capacitance 15 to the standard capacitance of the measuring capacitance decreases and capacitance changing part of the measuring capacitance is sufficiently reflected in output $V_{out}$. Furthermore, by supplying the electric current to the measuring capacitance from the amplifier 2 through the capacitance to cancel the standard capacitance, the electric current that flows through the feedback capacitance 15 decreases, in other words, the offset part of the electric current that flows through the feedback capacitance decreases and therefore it is possible to raise the gain of the capacitance measurement apparatus decided by $C_f$.

As a result, in the capacitance measurement apparatus according to the first embodiment, even in the case of fixing the electric potential of the signal line 17 that connects the measuring capacitance 14 and the fixed capacitance 15, since the sensibility of the capacitance measurement apparatus does not decrease, it is possible to execute an accurate capacitance measurement.

The first embodiment is explained below using expressions.

For a start, the output $V_a$ of the voltage supply circuit can be represented by $$V_a=R_{a2}(AV_o-V_s)/(R_{a1}+R_{a2}) \qquad (8)$$

Here, assume that A=2, $V_s=0$ and $R_{a1}=R_{a2}$ for simplicity. At this time, since it is set up to be $V_a=V_{in}$ ($V_a$ and $V_{in}$ are same electric potential), it is all right to be $$V_o=V_{in} \qquad (9)$$

Consequently, the electric current $I_c$ that flows through the capacitance to cancel the standard capacitance $C_c$ can be represented by $$I_c=d\{C_c(AV_o-V_{in})\}/dt=d(C_cV_{in})/dt \qquad (10)$$

Next, since the operational amplifying circuit 12 is in the state of imaginary short, the voltage $V_{in}$ (the operation signal) from the altering voltage generator 13 is applied to the signal line 17. By so doing, the electric current flows through the detecting capacitance 14. This electric current $I_a$ can be represented by $$I_s=d(C_sV_{in})/dt=(C_d\omega_{in}\cos\omega_{in}t+C\omega_c\cos\omega_c t\cdot\sin\omega_{in}t+C\omega_{in}\sin\omega_c t\cdot\cos\omega_{in}t)V \qquad (11)$$

Here, $C_d$ is the standard capacitance value of the detecting capacitance 14, C is the amplitude of change capacitance of the measuring capacitance 14, $\omega_c$ is the angular frequency of capacitance change, V is the amplitude of the operation signal, and $\omega_{in}$ is the angular frequency of the operation signal.

Moreover, the electric current $I_f$ that flows through the feedback capacitance C f can be represented by $$I_f=d\{C_f(V_{out}-V_{in})\}/dt \qquad (12)$$

Here, since the input impedance of the operational amplifying circuit 12 is sufficiently high, and it is set up to be $V_a=V_{in}$, and $R_{a1}$ and $R_{a2}$ are sufficiently high resistance values, the electric current does not flow through $R_{a1}$ and $R_{a2}$ and therefore $I_c$, $I_s$, and $I_f$ have the following relationship:

$$I_f=I_s-I_c \qquad (13)$$

$$d\{C_f(V_{out}-V_{in})\}/dt=d(C_sV_{in})/dt-d(C_cV_{in})/dt \qquad (14)$$

Consequently, the output $V_{out}$ of the signal output terminal 18 is $$V_{out}=\{1+(C_s-C_c)/C_f\}V_{in}=\{1+(C_d+C\sin\omega_c t-C_c)/C_f\}V\sin\omega_{in}t \qquad (15)$$

Under these conditions (A=2, $V_s=0$ and $R_{a1}=R_{a2}$), by making $C_c$ equal to $C_d$, it is possible to preclude the influence of the standard capacitance of the detecting capacitance 14 to circuit output. In other words, out of the detecting capacitance 14 only the signal that corresponds to the change capacitance is outputted to the circuit output. In sum, in this case, since the circuit output can be represented by $$V_{out}=(1+C\sin\omega_c t/C_f)V\sin\omega_{in}t \qquad (16),$$

the standard capacitance does not influence the circuit output and therefore it is possible to measure the capacitance change C accurately with high sensibility.

In the foregoing, explanation is made focusing on the attention on the electric current; the confirmation is given below focusing on the voltage.

Since the input impedance of the operational amplifying circuit 12 is sufficiently high, and it is set up to be $V_a=V_{in}$, and $R_{a1}$ and $R_{a2}$ are sufficiently high resistance values, the electric current does not flow through $R_{a1}$ and $R_{a2}$ and therefore the electric charge quantity of the signal line is constant. Consequently, $$C_c V_{in} + C_f (V_{out} - V_{in}) = C_s V_{in} \qquad (17)$$

$$V_{out} = \{1+(C_s-C_c)/C_f\}V_{in} = \{1+(C_d+C\sin\omega_c t-C_c)/C_f\}V\sin\omega_{in} t \qquad (18)$$

This is same as the above-mentioned expression of $V_{out}$. Consequently, in the embodiment shown in FIG. 3, under the above-mentioned conditions, it is possible to execute a correct capacitance measurement.

Figure 5:
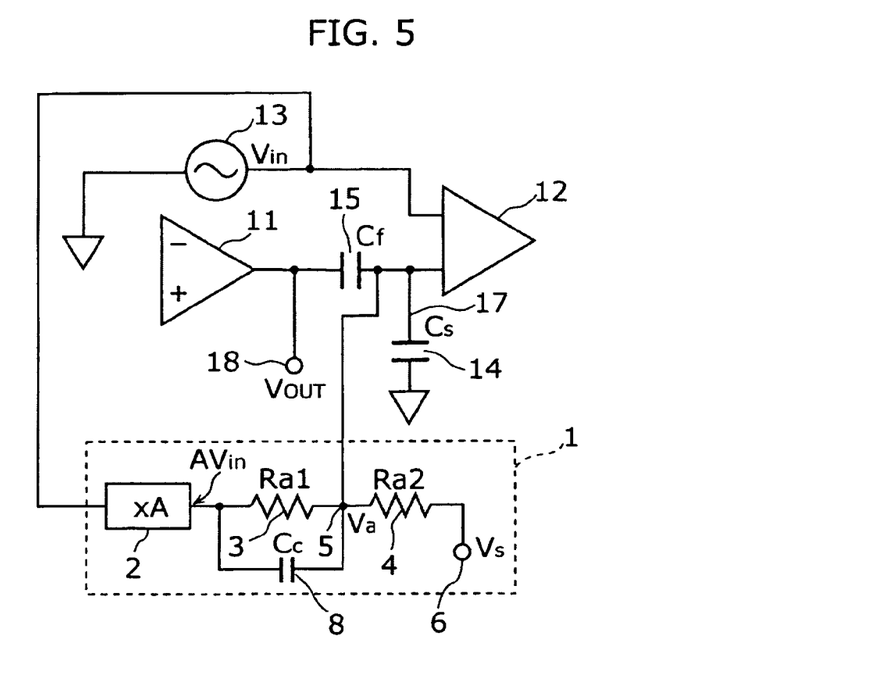
FIG. 5 is a circuit diagram that shows a capacitance measurement apparatus including an electric potential fixing apparatus according to the second embodiment of the present invention.

FIG. 5 is a circuit diagram that shows a capacitance measurement apparatus equipped with an electric fixing/standard capacitance cancel means including a voltage supply circuit according to the second embodiment of the present invention. In this voltage supply circuit 1 according to the second embodiment, the AC voltage generator 13 to apply the operation signal $V_{in}$ to the signal line 17 instead of the AC voltage generator 7 is connected to the input side of the amplifier 2 in the configuration according to the above-mentioned first embodiment. By the way, the other configuration according to the second embodiment is similar to the first embodiment.

In the second embodiment, as is described above, by connecting the AC voltage generator 13 to apply the operation signal $V_{in}$ to the signal line 17 with the input side of the amplifier 2, it is possible to omit the AC voltage generator 7 according to the first embodiment, and therefore it is possible to simplify the circuit configuration compared with the first embodiment.

Additionally, in the second embodiment, similarly to the above-mentioned first embodiment, by adjusting the amplitude A of the amplifier 2, the resistance value $R_{a1}$ of the first high resistance 3, the resistance value $R_{a2}$ of the second high resistance 4, and the voltage $V_s$ of the terminal 6, it is possible to easily set up the voltage $V_a$ in the output terminal 5 of the voltage supply circuit 1 to be equal to the voltage $V_{in}$ of the operation signal of the signal line 17. Additionally, by adjusting the amplitude A of the amplifier 2 and the capacitance value $C_c$ of the capacitance to cancel the standard capacitance, it is possible to set up cancel quantity of the measuring capacitance. More specifically, it is possible to cause the amplitude A to be A=2 by making the resistance values of resistance 22 and 23 of the amplifier 2 shown in FIG. 4 $R_1$'$R_2$; it is possible to cause easily the voltage Va of the output terminal 5 of the voltage supply circuit 1 to be equal electric potential to the voltage $V_{in}$ by making $V_s$=0 V, and $R_{a1}=R_{a2}$. Furthermore, when the standard capacitance of the detecting capacitance 14 is $C_c=C_d$ and the amplitude of the amplifier 2 is A=2, as described above, all the electric current that flows through the standard capacitance in the detecting capacitance is supplied by the standard capacitance cancel capacitance, only the electric current that flows through the change capacitance component flows through the feedback capacitance 15 and therefore the standard capacitance value does not influence the output $V_{out}$.

In addition, the embodiments disclosed this time should be thought to be exemplification in all respects and not to be limited. The scope of the present invention is shown not by the above-described explanation of the embodiments but by the scope of claims and further all changes in the scope of claims and in the meaning and scope of uniformity are included.

For example, in the above-described embodiments, the first high resistance 3 and the second high resistance 4 are used as the high impedance of the voltage supply circuit 1, but the present invention is not limited to this. It is acceptable, for example, to use the reverse bias characteristic of diode as the high impedance and it is possible to use an off state of a transistor. In other words, the high impedance and the high resistance have the same function to work as the resistance component.

Figure 6:
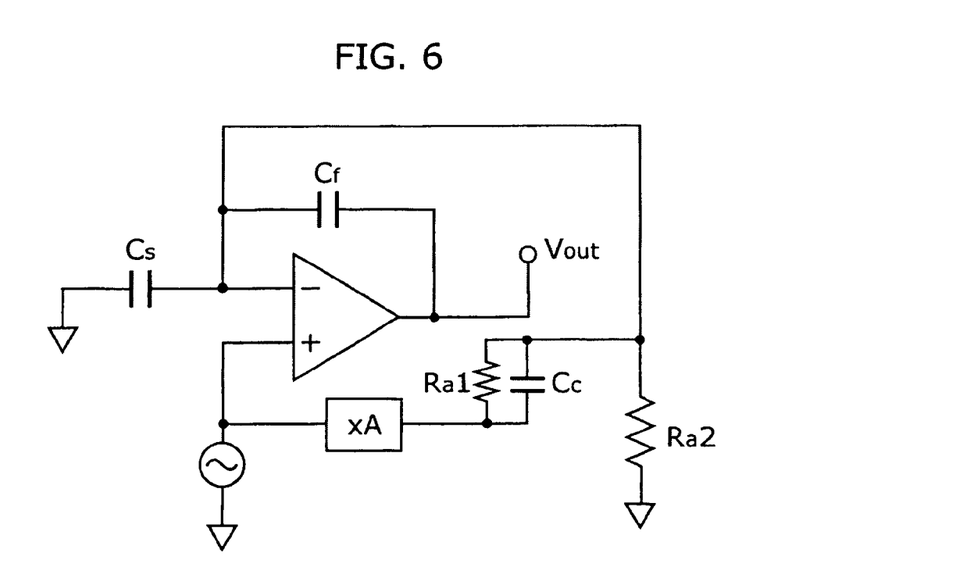
FIG. 6 is a circuit diagram that shows a capacitance measurement apparatus including an electric potential fixing apparatus according to another embodiment of the present invention.

In FIG. 3 and FIG. 5, the circuit is configured with two operational amplifying circuits but it is acceptable to configure the circuit with one operational amplifying circuit as in FIG. 6. Furthermore, 12 is configured with the operational amplifying circuit but it is acceptable to configure 12 with an impedance exchange.

Moreover, in the above-described embodiments, the capacitance measurement apparatus with the circuit configuration shown in FIG. 3 and FIG. 5 is explained, but the present invention is not limited to this and similarly applicable to a capacitance measurement apparatus with another circuit configuration.

Additionally, in the above-described embodiments, a case of fixing the electric potential of the signal line 17 that connects the measuring capacitance 14 and the fixed capacitance 15 in the capacitance measurement apparatus is explained, but the present invention is not limited to this and widely applicable to a case of fixing the electric potential of a apparatus other than the capacitance measurement apparatus including a circuit configuration where the first capacitance and the second capacitance are directly connected.

As is described above, by the present invention, in the case of fixing the electric potential of the connection line between the first capacitance and the second capacitance, it is possible to prevent the electric charge quantity of the connection line between the first capacitance and the second capacitance from changing. Furthermore, since at least part of the electric current that flows through the measuring capacitance can be supplied through the capacitance to cancel the standard capacitance, it is possible to sufficiently cover the capacitance change that takes place in the output $V_{out}$. As a result, for example, in the case of fixing the electric potential of the connection line between the first capacitance and the second capacitance in the capacitance measurement apparatus, the sensibility of the capacitance measurement apparatus does not decrease and therefore it is possible to execute an accurate capacitance measurement with high sensibility.

Industrial Applicability

The electric potential fixing apparatus according to the present invention can be used as a capacitance measurement apparatus and a capacitance detection apparatus to measure the capacitance value of the capacitive sensor whose electrostatic capacitance changes in response to the received physical quantity and particularly as the capacitance measurement apparatus equipped with the electric potential fixing/standard capacitance cancel circuit that cancels the standard capacitance of the capacitive sensor and as the electric potential fixing circuit for a microphone apparatus included in a small and light apparatus such as a cell phone.

The invention claimed is:

1. An electric potential fixing apparatus that is connected to a connection line between two capacitances, a first capacitance that is a measuring capacitance and a second capacitance that is directly connected to the first capacitance comprising:
   an output terminal that is connected to the connection line;
   a voltage supply unit operable to maintain constantly electric potential of the connection line between the two capacitances, holding combined total electric charge quantity of the first capacitance and the second capacitance by supplying voltage to the connection line from the output terminal;
   an alternating-current voltage generator which generates an alternating-current voltage; and
   a first operational amplifier having an input terminal connected to the connection line and another input terminal connected to the alternating-current voltage generator;
   wherein the voltage supply unit includes a first high resistance and a second high resistance that is directly connected to the first high resistance; a voltage dividing unit that outputs electric potential divided by the first high resistance and the second high resistance to the output terminal; and a third capacitance that is connected in parallel to at least either of the first high resistance and the second high resistance.

2. An electric potential fixing apparatus that is connected to a connection line between two capacitances, a first capacitance that is a measuring capacitance and a second capacitance that is directly connected to the first capacitance comprising:
   an output terminal that is connected to the connection line;
   a voltage supply unit operable to output, to the connection line, electric potential that is equal to electric potential of an operation signal applied to the connection line;
   an alternating-current voltage generator which generates an alternating-current voltage; and
   a first operational amplifier having an input terminal connected to the connection line and another input terminal connected to the alternating-current voltage generator;
   wherein the voltage supply unit includes a first high resistance and a second high resistance that is directly connected to the first high resistance; a voltage dividing unit that outputs electric potential divided by the first high resistance and the second high resistance to the output terminal; and a third capacitance that is connected in parallel to at least either of the first high resistance and the second high resistance.

3. The electric potential fixing apparatus according to claim 1 or claim 2,
   wherein the voltage supply unit further includes an amplifier and a predetermined voltage applying unit,
   the amplifier is connected to a terminal of the first high resistance,
   the other terminal of the first high resistance and a terminal of the second high resistance are connected,
   the output terminal is connected between the other terminal of the first high resistance and the terminal of the second high resistance, and
   the other terminal of the second high resistance and the predetermined voltage applying unit are connected each other.

4. The capacitance measurement apparatus according to claim 1 or claim 2,
   wherein the electric potential fixing apparatus further comprises the second operational amplifier, and
   the output terminal of the second operational amplifier is connected to the second capacitance.

5. An electric potential fixing method for fixing electric potential of a connection line between two capacitances, a first capacitance and a second capacitance that is directly connected to the first capacitance, using a voltage supply unit which has an amplifier, a first high resistance and a second high resistance, and a third capacitance that is connected in parallel to at least either of the first high resistance and the second high resistance, the electric potential fixing method including;
   a step for outputting electric potential divided by the first high resistance and the second high resistance to the connection line between the two capacitances;
   a step for setting up electric potential of an operation signal that is applied to the connection line between the two capacitances and output electric potential of the voltage supply unit to become equal by adjusting an amplitude of the amplifier, values of the two high resistances and a value of a third capacitance.

6. The electric potential fixing method according to claim 5,
   wherein a terminal part of either the first high resistance or the second high resistance of the voltage supply unit includes a predetermined voltage applying unit, and the electric potential of an operation signal that is applied to the connection line between the two capacitances and the output electric potential of the voltage supply unit are set up to become equal by adjusting applied voltage of the predetermined voltage applying unit.

7. The electric potential fixing method according to claim 5,
   wherein either the first capacitance or the second capacitance is used as a measuring capacitance.

* * * * *